(12) United States Patent
Oren et al.

(10) Patent No.: US 7,608,084 B2
(45) Date of Patent: Oct. 27, 2009

(54) SUTURING INSTRUMENT AND METHOD

(76) Inventors: Ran Oren, Kibbutz Gaaton, Doar Na Oshrat, 25130 (IL); Dan Moor, Kibbutz Gaaton, Doar Na Oshrat, 25130 (IL)

( * ) Notice: Subject to any disclaimer, the term of this patent is extended or adjusted under 35 U.S.C. 154(b) by 376 days.

(21) Appl. No.: 10/947,139

(22) Filed: Sep. 23, 2004

(65) Prior Publication Data

US 2005/0043748 A1    Feb. 24, 2005

Related U.S. Application Data

(63) Continuation of application No. 09/994,882, filed on Nov. 28, 2001, now abandoned, which is a continuation-in-part of application No. 09/722,712, filed on Nov. 28, 2000, now Pat. No. 6,511,487.

(51) Int. Cl.
    *A61B 17/04* (2006.01)
(52) U.S. Cl. ..................................... 606/144
(58) Field of Classification Search ......... 606/144–150, 606/139
    See application file for complete search history.

(56) References Cited

U.S. PATENT DOCUMENTS

| | | |
|---|---|---|
| 1,815,725 A | 7/1931 | Pilling et al. |
| 1,822,330 A | 8/1931 | Ainslie |
| 1,856,721 A | 5/1932 | Nagelman |
| 1,918,700 A | 7/1933 | Harris |
| 1,933,024 A * | 10/1933 | Nagelmann .............. 606/145 |
| 2,269,963 A | 1/1942 | Wappler |
| 2,577,240 A | 12/1951 | Findley |
| 2,738,790 A | 3/1956 | Todt, Sr. et al. |
| 3,842,840 A | 10/1974 | Schweitzer |
| 3,946,740 A | 3/1976 | Bassett |
| 4,109,658 A | 8/1978 | Hughes |
| 4,164,225 A | 8/1979 | Johnson et al. |
| 4,345,601 A | 8/1982 | Fukuda |
| 4,493,323 A | 1/1985 | Albright et al. |
| 4,621,640 A | 11/1986 | Mulhollan et al. |
| 4,635,637 A | 1/1987 | Schreober |
| 4,644,953 A | 2/1987 | Lahodney et al. |
| 4,738,255 A | 4/1988 | Goble et al. |
| 4,741,330 A | 5/1988 | Hayhurst |
| 4,836,205 A | 6/1989 | Barrett |
| 4,923,461 A | 5/1990 | Caspari et al. |
| 4,926,860 A | 5/1990 | Stice et al. |
| 4,935,027 A | 6/1990 | Yoon |

(Continued)

FOREIGN PATENT DOCUMENTS

DE        245576        4/1912

(Continued)

OTHER PUBLICATIONS

International Preliminary Report on Patentability Dated Oct. 2, 2008 From the International Bureau of WIPO Re.: Application No. PCT/IL2007/000335.

(Continued)

*Primary Examiner*—(Jackie) Tan-Uyen T. Ho
*Assistant Examiner*—Gregory Anderson

(57) ABSTRACT

Tissue suturing instruments and methods of using same are provided. The tissue suturing instruments are designed and configured for suturing tissue grasped thereby to soft tissue as well as to hard tissue.

18 Claims, 4 Drawing Sheets

U.S. PATENT DOCUMENTS

| | | | |
|---|---|---|---|
| 5,037,422 A | | 8/1991 | Hayhurst |
| 5,046,513 A | | 9/1991 | Gatturna et al. |
| 5,059,201 A | * | 10/1991 | Asnis .................. 606/144 |
| 5,085,661 A | | 2/1992 | Moss |
| 5,304,184 A | | 4/1994 | Hathaway et al. |
| 5,342,389 A | | 8/1994 | Haber et al. |
| 5,417,699 A | | 5/1995 | Klein et al. |
| 5,454,823 A | | 10/1995 | Richardson et al. |
| 5,522,820 A | | 6/1996 | Caspari et al. |
| 5,609,597 A | | 3/1997 | Lehrer |
| 5,613,974 A | | 3/1997 | Andreas et al. |
| 5,645,552 A | | 7/1997 | Sherts |
| 5,665,108 A | | 9/1997 | Galindo |
| 5,683,401 A | | 11/1997 | Schmieding et al. |
| 5,730,747 A | | 3/1998 | Ek et al. |
| 5,741,281 A | | 4/1998 | Martin |
| 5,776,150 A | | 7/1998 | Nolan et al. |
| 5,779,719 A | | 7/1998 | Klein et al. |
| 5,843,099 A | | 12/1998 | Nichols et al. |
| 5,980,538 A | * | 11/1999 | Fuchs et al. .................. 606/145 |
| 6,051,006 A | | 4/2000 | Shluzas et al. |
| 6,071,289 A | | 6/2000 | Stefanchik et al. |
| 6,129,741 A | | 10/2000 | Wurster et al. |
| 6,511,487 B1 | | 1/2003 | Oren et al. |
| 6,551,330 B1 | * | 4/2003 | Bain et al. .................. 606/144 |
| 6,770,084 B1 | * | 8/2004 | Bain et al. .................. 606/144 |
| 2004/0138682 A1 | | 7/2004 | Onuki et al. |

FOREIGN PATENT DOCUMENTS

| | | |
|---|---|---|
| WO | WO 99/56573 | 11/1999 |
| WO | WO 02/43558 | 6/2002 |

OTHER PUBLICATIONS

Office Action Dated Jun. 24, 2007 From the Israeli Patent Office Re.: Application No. 156014.

International Search Report Dated Jul. 30, 2007 From the International Searching Authority Re.: Application No. PCT/IL2007/000335.

Supplementary Partial European Search Report Dated Feb. 26, 2009 From the European Patent Office Re.: Application No. 01998258.6.

Written Opinion Dated Jul. 30, 2007 From the International Searching Authority Re.: Application No. PCT/IL2007/000335.

* cited by examiner

SUTURING INSTRUMENT AND METHOD

RELATED PATENT APPLICATIONS

This is a continuation of U.S. patent application Ser. No. 09/994,882 filed 28 Nov. 2001, now abandoned which is a Continuation-in-Part of U.S. patent application Ser. No. 09/722,712, filed 28 Nov. 2000, now U.S. Pat. No. 6,511,487.

FIELD AND BACKGROUND OF THE INVENTION

The present invention relates to suturing instruments useful in surgery, and also to a method of applying a suture to tissue during surgery.

Many surgical procedures are presently being performed via an endoscope in order to minimize the size of the incisions and the trauma to the patient. In such procedures, the surgical instrument is generally introduced through a cannula or passageway in the endoscope while the surgeon views the surgical site through another passageway in the endoscope. A number of forceps-type suturing instruments have been designed for introduction through a cannula used in endoscopic procedures. One such forceps-type suturing instrument is disclosed in U.S. Pat. Nos. 5,730,747 and 6,051,006. The known suturing instruments of this type, however, are generally of relatively complicated construction and/or are useful only with respect to needled sutures.

OBJECTS AND SUMMARY OF THE INVENTION

An object of the present invention is to provide a suturing instrument of relatively simple construction and which can be used with unneedled sutures, i.e., suture threads per se, i.e., without a puncturer being attached to the suture.

Another object of the invention is to provide a suturing instrument particularly useful as a forceps type instrument for introduction through a cannula used in endoscopic procedures. A further object of the invention is to provide a novel method of applying a suture to tissue.

According to one aspect of the invention in the present application, there is provided a tissue suturing instrument comprising: a tissue grasping mechanism including a static grasping member and a pivotally mounted grasping member designed and configured for grasping a tissue, one of the grasping members carrying a suture holder for positioning a suture on a first side of the tissue grasped thereby; a crochet head slidable in a linear path through a forward stroke and a return stroke, the crochet head being designed and configured for piercing through the tissue from a second side thereof during the forward stroke, engaging the suture following the piercing, and drawing the suture through the tissue during the return stroke; and a frame assembly including a proximal section fonned with a first handle and a distal section carrying the tissue grasping mechanism and the crochet head, the proximal section and the distal section being connected by an elongated shank.

According to the preferred embodiment of the invention described below, the suture holder is in the form of a wall carried by the one grasping member at an angle thereto and formed with an opening through which the crochet head moves during the forward stroke.

According to a further feature in the described preferred embodiment, the static member carries a guide for guiding the sliding movement of the crochet head through its forward and return strokes.

According to another aspect of the present invention, there is provided a method of applying a suture to tissue comprising: providing a tissue suturing instrument comprising (a) a tissue grasping mechanism including a static grasping member and a pivotally mounted grasping member designed and configured for grasping a tissue, one of the grasping members carrying a suture holder for positioning a suture on a first side of the tissue grasped thereby; (b) a crochet head slidable in a linear path through a forward stroke and a return stroke, the crochet head being designed and configured for piercing through the tissue from a second side thereof during the forward stroke, engaging the suture following the piercing, and drawing the suture through the tissue during the return stroke; and (c) a frame assembly including a proximal section formed with a first handle and a distal section carrying the tissue grasping mechanism and the crochet head, the proximal section and the distal section being connected by an elongated shank applying a suture to the suture holder such that the suture is on one side of the tissue to be sutured, and the grasping members and crochet head are on the opposite side of the tissue to be sutured; pivoting the first handle to cause the crochet head to move from the opposite side to the one side, to pierce the grasped tissue, and to engage the suture on the one side; and returning the first handle to cause the crochet head to move with the suture from the one side to the opposite side.

As will be described more particularly below, the foregoing features enable suturing instruments to be constructed with a relatively few simple parts and to be used with unneedled sutures.

Further features and advantages of the invention will be apparent from the description below.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
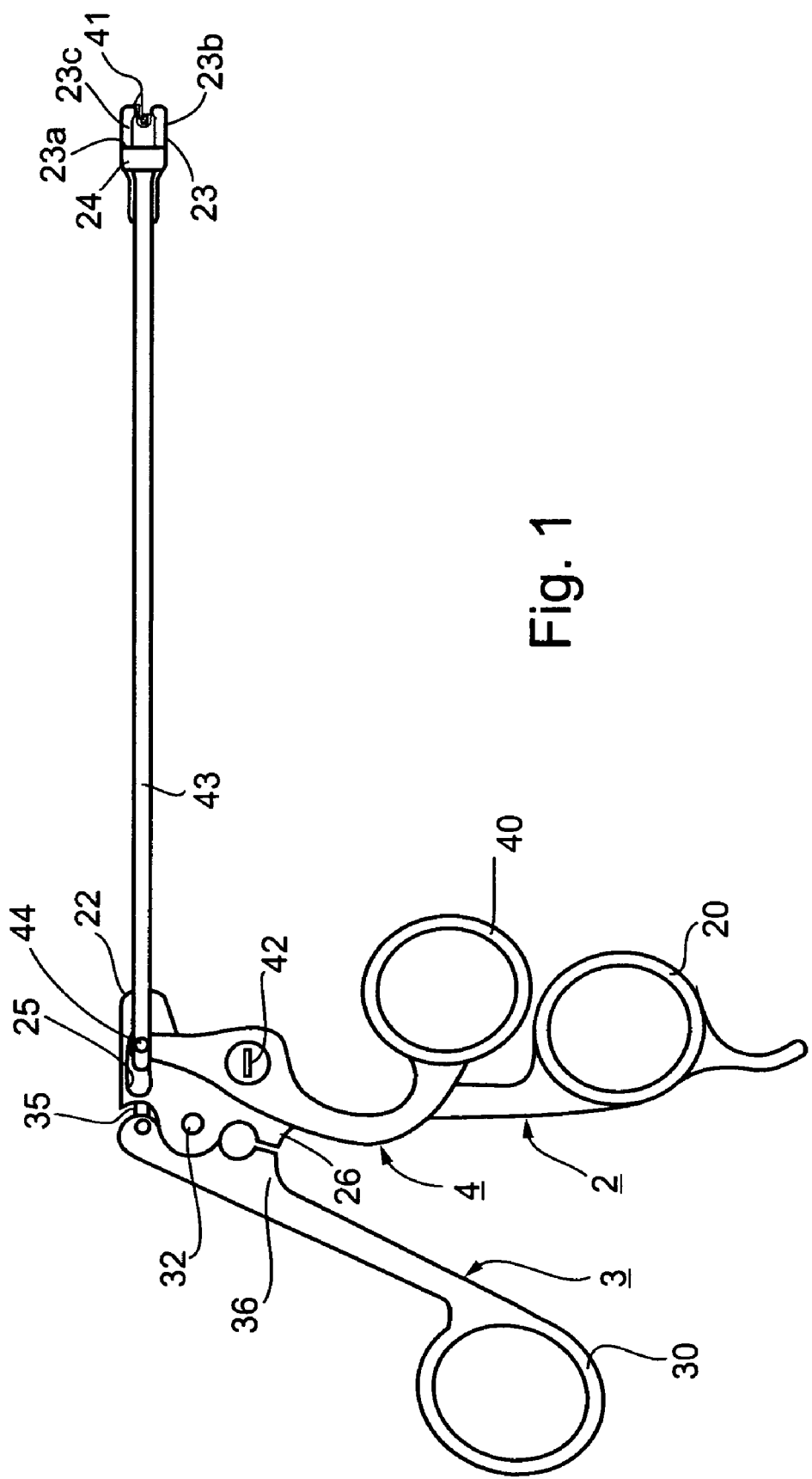
FIG. 1 is a side view illustrating a preferred embodiment of a suturing instrument constructed in accordance with the present invention.

The present invention is of suturing devices and methods which can be used to efficiently insert a suture in tissue during surgery. Specifically, the present invention can be used in minimally invasive, endoscope, laparoscope or arthroscope assisted surgeries.

The principles and operation of a device and method according to the present invention may be better understood with reference to the drawings and accompanying descriptions.

Before explaining the invention in detail, it is to be understood that the invention is not limited in its application to the details of construction and the arrangement of the components set forth in the following descriptions or illustrated in the drawings. The invention is capable of other embodiments or of being practiced or carried out in various ways. Also, it is to be understood that the phraseology and terminology employed herein is for the purpose of description and should not be regarded as limiting.

FIG. 1, illustrates one configuration of a suturing device/ instrument according to the present invention.

The suturing instrument illustrated in FIG. 1 is of the forceps type particularly useful by applying it through a cannula used in endoscopic procedures in order to suture tissue at the surgical site.

Figure 2:
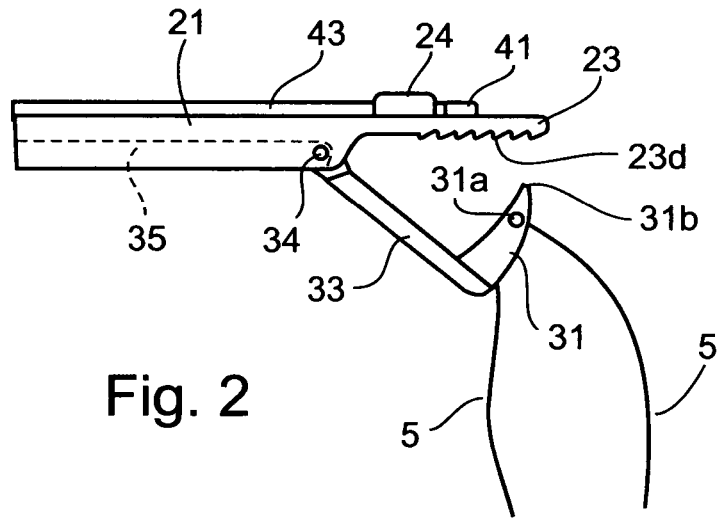
FIG. 2 is an enlarged bottom view of the distal end of the suturing instrument of FIG. 1, illustrating the puncturer in its open position for receiving a suture.

This configuration of the suturing instrument is composed of three main assemblies:

(1) a frame assembly, generally designated 2, including a first handle 2 at one end (hereinafter called the proximal end), fixed substantially perpendicularly to an elongated shank 21 (FIG. 2);

(2) a puncturer assembly, generally designated 3, including a second handle 30 at the proximal end of the instrument, pivotally mounted to the frame assembly 2 and coupled to a puncturer 31 (FIG. 2) pivotally mounted at the distal end of the elongated shank 21; and (3) a crochet head assembly, generally designated 4, including a third handle 40 also pivotally mounted to the frame assembly 2 and coupled to a slidable crochet head 41 at the distal end of the elongated shank 21.

As will be described more particularly below, the suture, shown at 5 in FIG. 2, is loaded onto the puncturer 31 when in its open position as illustrated in FIG. 2.

With respect to the frame assembly 2, the proximal end of the elongated shank 21 is fixed within a perpendicular extension 22 at the upper end of handle 20. The distal end of the elongated shank 21 carries a fixed jaw 23 formed with a pair of legs 23a, 23b parallel to the axis of the elongated shank 21 and spaced from each other to define a space 23c. As shown particularly in FIG. 2, the inner surface of jaw 23 facing the pivotal puncturer 31 is ribbed as shown at 23d in order to firmly grasp the tissue to be sutured between it and the pivotal puncturer, as will be described below.

The distal end of the elongated shank 21 further includes a U-shaped member 24 serving as a guide for a part of the crochet head assembly 4, as will be described below. In addition, extension 22 of handle 20 is formed with a slot 25 (FIG. 1) at the proximal end of the elongated shank 21, for accommodating a coupling element of the crochet head assembly 4 as will also be described below. Further, the upper end of handle 20 of the frame assembly 2 includes an abutment 26 serving as a stop for limiting the pivotal movement of handle 30 of the puncturer assembly 3.

With respect to the puncturer assembly 3, handle 30 of that assembly is pivotally mounted at 32 to the upper end of handle 20 of the frame assembly 2. As shown particularly in FIG. 2, puncturer 31 pivotally mounted at the distal end of the elongated shank 21, is formed with a hole 31a for receiving the suture 5, and with a pointed tip 31b for piercing the tissue clamped between it and the ribbed surface 23d of the fixed jaw 23.

Puncturer 31 is pivotally mounted to the distal end of the elongated shank 21 by an arm 33 carrying the puncturer 31 at one end, and pivotally mounted at its opposite end 34 to the elongated shank 21. Arm 33 is coupled to the upper end of handle 30 of the puncturer assembly 3 by a rod 35 (FIG. 1) passing through, or alongside of, the elongated shank 21. The arrangement is such that pivoting handle 30 away from handle 20 pivots puncturer 31 to its open position illustrated in FIG. 2 for receiving the suture 5, and pivoting handle 30 towards handle 20 moves puncturer 31 through the opening 23c in the jaw 23 to pierce the tissue clamped between the puncturer and the jaw, and to bring the suture 5 to the opposite side of the jaw. Handle 30 is formed on its inner face with an abutment 36 engagable with abutment 26 of handle 20 to limit the latter pivotal movement of handle 30.

With respect to the crochet head assembly 4, its handle 40 is pivotally mounted at 42 to the upper end of handle 20 of the frame assembly 2. Preferably, this pivotal mounting includes a piano spring (not shown) to bias the handle 40 to the position illustrated in FIG. 1, which is the retracted position of the crochet head 41.

The crochet head 41 is carried at the distal end of a slide 43 extending along one side of the elongated shank 21. The proximal end of slide 43 is coupled by a pin 44 (FIG. 1) to the upper end of handle 40. Pin 44 is movable within slot 25 in the extension 22 at the upper end of handle 20 to limit the pivotal movements of handle 40 with respect to handle 20. As will be described below, handle 40 may be pivoted with respect to handle 20 to move slide 43, and the crochet 41 carried at the distal end of the slide, through forward and return strokes parallel to the longitudinal axis of the elongated shank 21. The forward and return movements of the slide 43 are guided by the U-shaped member 24 at the distal end of the elongated shank.

Figure 3:
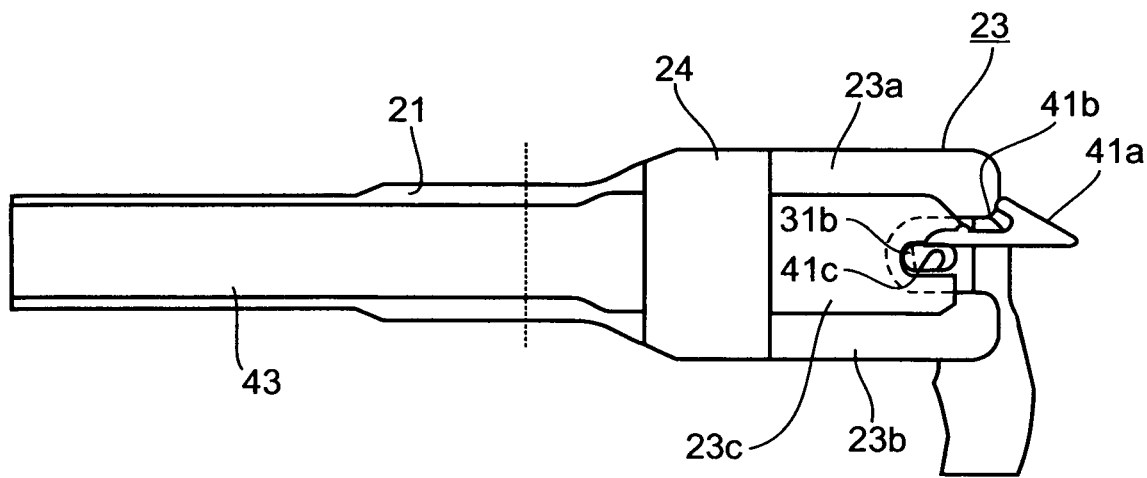
FIG. 3 is an enlarged side view of the distal end of the suturing instrument of FIG. 1 with the crochet head in its extended position.

The structure of the crochet head 41 is more particularly illustrated in FIG. 3. It includes a tapered nose 41a at one end for engaging the suture 5 during the forward movement of the crochet head, and a hook formation at the opposite end for receiving the suture and for clamping it to the jaw 23 during the return movement of the crochet head. The crochet head is further formed with an axial slot 41c to accommodate the pointed tip 31b of the puncturer 31 when the puncturer is pivoted to its closed position and the crochet has been moved to its most forward position.

The illustrated suturing instrument may be used in the following manner.

First, handle 30 is pivoted away from handle 20 so as to pivot the puncturer 31 to its open position as shown in FIG. 2, to enable the suture 5 to be loaded thereon by passing the suture through opening 31a of the puncturer.

Handle 30 may then be pivoted towards handle 20 to move the puncturer 31, together with the portion of the suture carried thereby, to the closed position of the puncturer, i.e., through opening 23c of jaw 23. This enables the distal portion of the instrument to be inserted through the cannula (not shown) of the endoscope. After the distal portion of the instrument has passed through the cannula and is located in the surgical site, handle 30 may be pivoted away from handle 20 to return the puncturer to its open position, as shown in FIG. 2, preparatory to its use for suturing tissue. In this condition of the instrument, handle 40 is in the position shown in FIG. 1, such that the crochet head 41 actuated by the handle is in its retracted position on the proximal side of jaw 23.

The surgeon may then manipulate the instrument with the puncturer 31 in its open position to locate the puncturer on one side of the tissue to be sutured, and to locate the jaw 23 on the opposite side of the tissue to be sutured. The surgeon then moves handle 30 towards handle 20, which thereby, by virtue of the coupling rod 35, pivots puncturer 31 towards jaw 23 and then through the opening 23c in the jaw, to thereby pierce the tissue and to bring the portion of suture 5 within the needle hole 31a to the opposite side of the jaw. While the puncturer is in its closed position, handle 40 is then pivoted clockwise to move the crochet head 41, coupled to the handle by slide 43, through a forward stroke parallel to the elongated shank 21 from the proximal side of the jaw 23 to the distal side thereof, and then releases handle 40 to permit its spring bias to return the crochet head through a return stroke back to its initial position at the proximal side of the jaw.

During the movement of the crochet head in the forward stroke, its nose 41a engages the suture that has been passed through opening 23c in jaw 23, and guides the suture to the hook portion 41b of the crochet head, such that when the crochet head returns during the return stroke back to its initial position, the hook portion 41b of the crochet head clamps the suture to the jaw 23. Handle 30 may then be moved away from handle 20 to pivot the puncturer 31 to its open position, and thereby to release the tissue. The instrument may then be used for applying another suture to another portion of the tissue by repeating the foregoing steps.

Figure 4:
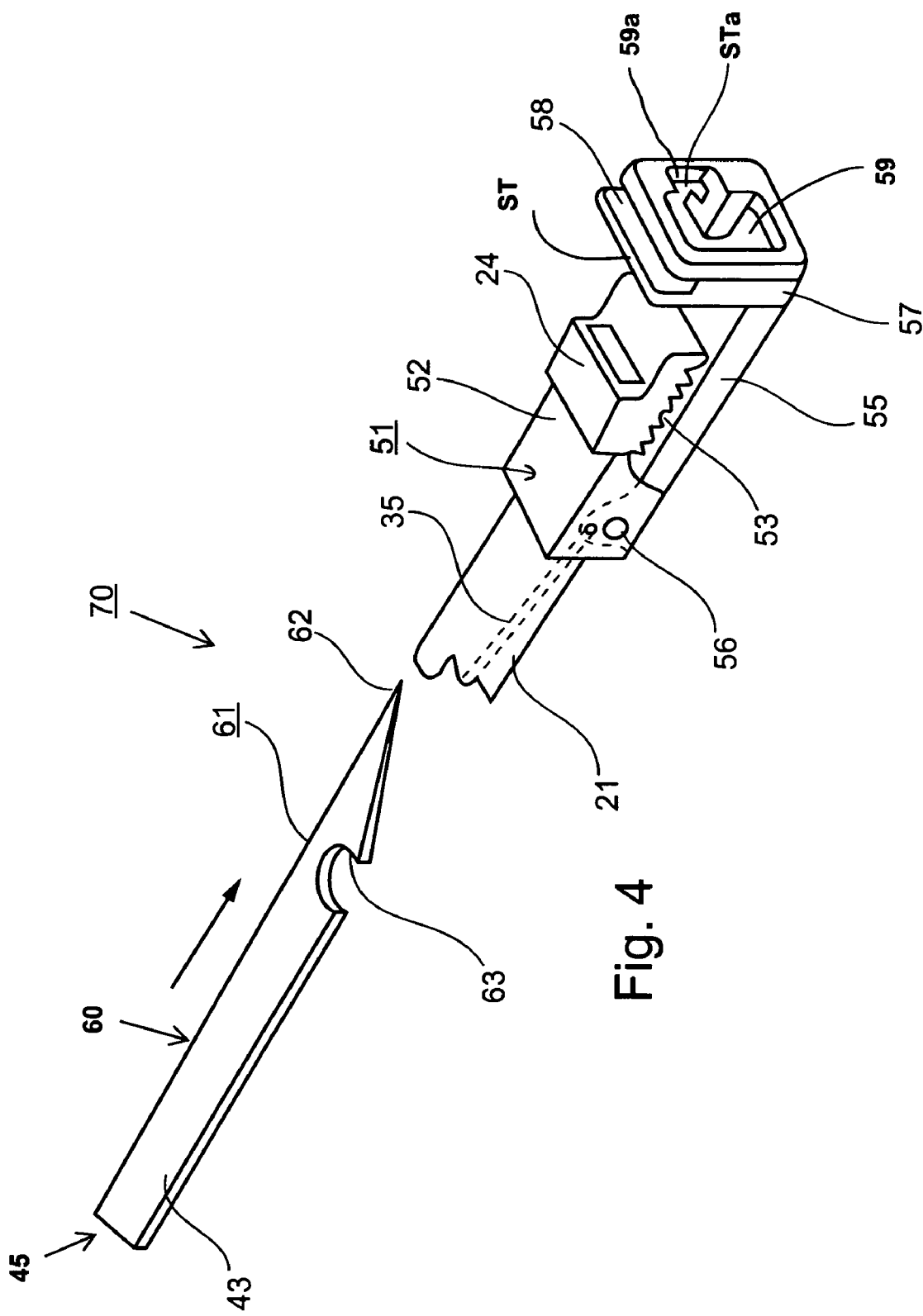
FIG. 4 is a perspective view of the distal end of an alternative embodiment of a suturing instrument constructed in accordance with the present invention, illustrating the grasping mechanism in its closed position.
Figure 5:
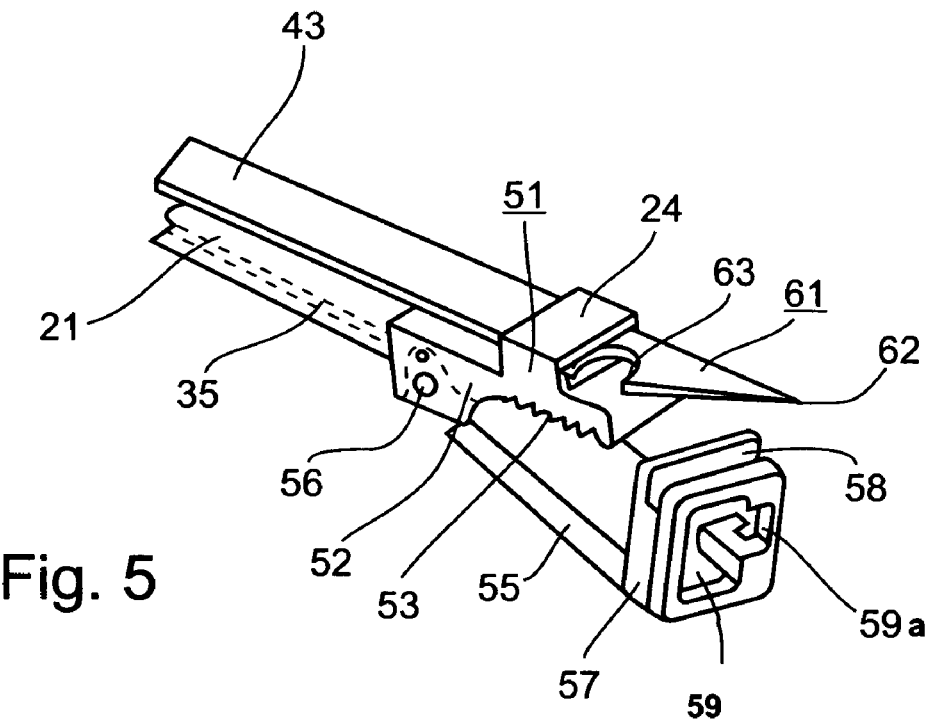
FIG. 5 is a perspective view of the distal end of the suturing instrument of FIG. 4 illustrating the grasping mechanism in its open position.
Figure 6:
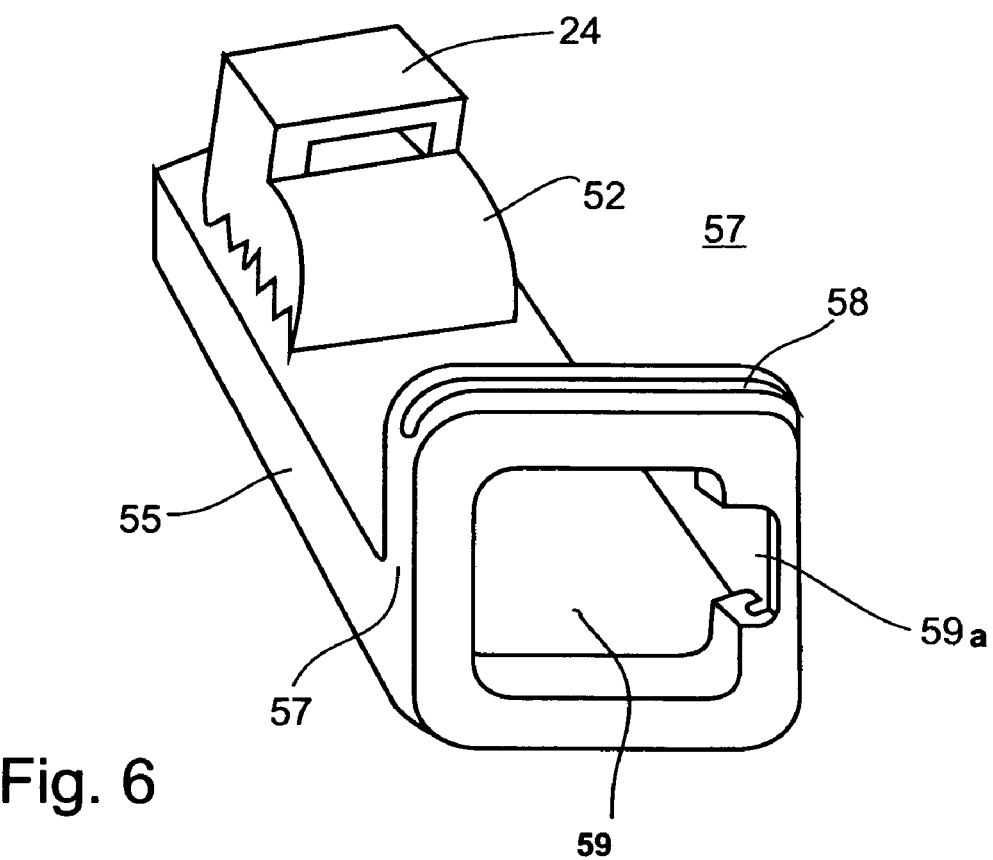
FIG. 6 is and end view of the movable grasping member of the suturing instrument of FIG. 4.

Reference is now made to FIGS. 4-6 which illustrate an alternative embodiment of the suturing instrument of the present invention which is referred to hereinunder as suturing instrument 45.

Suturing instrument 45 includes a frame assembly (not shown) which is substantially identical to frame assembly 2 shown in FIG. 1 and as such includes a first handle at the proximal end, fixed substantially perpendicularly to an elongated shank; a perpendicular extension at the upper end of the first handle which is formed with a slot for accommodating a coupling element; a second handle pivotally mounted to the upper end of the first handle; a coupling element for coupling the second handle to the tissue grasping elements; a first abutment at the upper end of the first handle serving as a stop for limiting the pivotal movement of the second handle; a second abutment at the upper end of the second handle engagable with the first abutment; a third handle pivotally mounted to the upper end of the first handle, preferably including a piano spring to bias the third handle to the position illustrated in FIG. 1; and a pin movable within a slot which couples a coupling slide to the upper end of the third handle. These components of suturing instrument 45 function similarly to those described hereinabove with respect to FIG. 1, and as such are numerically referenced hereinunder, in parentheses, with numbers used to identify similar components shown in FIG. 1.

In addition, suturing instrument 45 further includes a suturing head 70 which includes a separate tissue grasping mechanism and a piercing mechanism, exemplary configurations of which are further described hereinbelow with reference to FIGS. 4 and 5.

The function of suturing instrument 45 is distinguished from the function of the formerly described embodiment. Whereas the formerly described embodiment includes a puncturer assembly, shown as puncturer assembly 3 in FIG. 1, which grasps the tissue to be sutured, punctures the tissue and passes the suture through the tissue all in one movement, with a crochet head thereafter simply engaging the suture, suturing head 70 of the present embodiment has a tissue grasping mechanism 51 which is designed and configured for grasping a tissue and for positioning a suture on a first side of the tissue grasped thereby. Suturing head 70 further includes a separate crochet head 61 which is designed and configured for piercing through the tissue from a second side thereof and engaging the suture following piercing, thereafter enabling drawing the suture through the tissue.

Thus, in contrast to the formerly described embodiment, suturing instrument 45 includes separate piercing and grasping elements, which enable piercing the tissue and carrying the suture through the tissue following piercing thereof.

Such a suturing head 70 configuration provides a significant advantage in that it is capable of suturing tissues with a wide range of thicknesses, as there is no puncturer of a specific length to limit the thickness of the tissue capable of being sutured.

FIGS. 4 and 5 illustrate a detailed view of one preferred configuration of suturing head 70, illustrating in detail the construction of tissue grasping mechanism 51, hereinafter referred to as mechanism 51, and crochet head 61.

Mechanism 51 includes a static grasping member, hereinafter referred to as static member 52, and a movable grasping member, hereinafter referred to as movable member 55, both positioned at the distal end of suturing instrument 45.

Static member 52 is disposed rigidly on an elongated shank which is similar to shank 21 illustrated in FIG. 1. Movable member 55 is pivotally mounted to static member 52 by a pin, hereinafter referred to as pivot pin 56, passing through holes formed in both static member 52 and movable member 55 aligned coaxially. The holes in static member 52 and movable member 55 are sized such that pivot pin 56 is affixed by friction within the hole through static member 52 but is movable relative to the hole through movable member 55, allowing movable member 55 to rotate thereupon. Accordingly, movable member 55 is pivotally movable relative to static member 52.

As described above, mechanism 51 is designed and configured for grasping and holding a tissue to be sutured. Accordingly, static member 52 and movable member 55 each have a face disposed substantially opposite one another. The face of static member 52 which faces movable member 55 is formed with a series of parallel grooves therein and is hereinafter referred to as ribbed surface 53. Each groove of ribbed surface 53 is shaped and angled such that any tissue in contact therewith will be limited, preferably prevented, from moving with respect to static member 52.

The pivotal movement of movable member 55 serves to move the face of movable member 55 both closer to, and farther from, ribbed surface 53. The movement of movable member 55 is controlled by the movement of the second handle and a coupling rod, which are similar in function to handle 30 and coupling rod 35 described hereinabove with respect to FIG. 1. Accordingly, the pivotal motion of handle (30), transmitted by coupling rod (35), will cause movable member 55 to pivot with respect to static member 52 in a jawlike manner, the closing motion being for grasping the tissue to be sutured, the opening motion being for releasing the tissue. FIG. 4 depicts grasping mechanism 51 in a closed position. FIG. 5 depicts grasping mechanism 51 in an open position.

Mechanism 51 is also designed and configured for positioning a suture on a first side of a tissue to be sutured.

Reference is now made to FIG. 6 which shows a detailed view of the distal end of movable member 55. According to the alternative embodiment, movable member 55 has a distal end positioned substantially perpendicular to the face opposite static member 52 in the direction of static member 52. This angular end of movable member 55 is hereinafter referred to as suture holder 57. Suture holder 57 is preferably square or rectangular in shape, although it is appreciated that suture holder 57 may be of any shape appropriate for the relevant tissue to be sutured.

Suture holder 57 is formed with a groove along its circumference, or a portion of its circumference, hereinafter referred to as suture groove 58. Suture groove 58 is sized so as to accept an appropriate suturing material. Accordingly, the previously described closing motion of movable member 55 serves to position a suture disposed within suture groove 58 on a (first) side of a tissue grasped by mechanism 51.

Suture holder 57 is also formed with an opening therein, hereinafter opening 59, that is sized to allow crochet head 61 to pass therethrough. Opening 59 is shaped and positioned within suture holder 57 such that one of its sides extends toward the circumference of suture holder 57 beyond the depth of suture groove 58. Accordingly, at the location that opening 59 approaches the circumference of suture holder 57, suture groove 58 is exposed to the inside of opening 59 such that a suture disposed therein is accessible from within opening 59.

Suturing head 70 further includes crochet head 61, designed and configured for piercing through a tissue grasped by mechanism 51, engaging the suture and drawing the suture through the tissue. Crochet head 61 is part of a crochet head assembly 60 which also includes a third handle and coupling slide (similar to coupling slide 43 shown in FIG. 1). The movement of coupling slide 43 and crochet head 61 is controlled by the movement of the third handle, which is similar in function to handle 40 described hereinabove with respect to FIG. 1.

Crochet head 61 is formed with a sharp point for piercing a tissue to be sutured, hereinafter referred to as point 62, and a hooklike formation, hereinafter referred to as hook 63, designed to deflect a suture as crochet head 61 first passes the suture when moving in the direction of its extended position and to engage the suture as it subsequently passes the suture moving in a reverse direction toward its retracted position.

Crochet head 61 is carried at the distal end of coupling slide 43. Coupling slide 43, which includes an element slidable with respect to elongated shank 21, is coupled to the upper end of handle (40). Handle (40) is pivotally mounted to the first handle, which is similar in function to handle 20 described hereinabove with respect to FIG. 1. Handle (20) is preferably spring biased (spring not shown) to return handle (40) to the position whereby crochet head 61 is in its retracted position. The movement of crochet head 61 is controlled by the movement of handle (40) and coupling slide 43 in substantially the same manner as previously described with reference to FIG. 1.

Accordingly, the pivotal motion of handle (40) with respect to handle (20) will cause crochet head 61 to move through forward and return strokes substantially parallel to the longitudinal axis of elongated shank (21). Crochet head 61 is slidably mounted in proximity to mechanism 51 and is movable in a linear path through a forward stroke from a retracted position at the proximal end of mechanism 51 to an extended position beyond suture holder 57, and through a return stroke back to the retracted position. The forward stroke of crochet head 61 is for piercing the tissue held by mechanism 51 and the return stroke of crochet head 61 is for engaging the suture and drawing it through the tissue.

The forward and return movements of crochet head 61 are guided by an inverted U-shaped guide member (similar to member 24 of FIG. 1) which is formed as part of static member 52. Guide member 24 guides point 62 to pass within opening 59 at a point where opening 59 approaches the circumference of suture holder 57 beyond the depth of suture groove 58 such that crochet head 61 passes between the circumference of opening 59 and a suture disposed within suture groove 58. As described above, the deployment of handles (20, 30 and 40) proximal to one another allows suturing instrument 45 to be easily employed by a user. Once the suture is disposed on suture head 70, a user may preferably operate each of the handles in proper sequence by the fingers of one hand, as follows.

First, a suture is disposed within suture groove 58. Thereafter, suturing instrument 45 is preferably held with the middle finger in the loop of handle (20), the index finger in the loop of handle (40) and the thumb in the loop of handle (30). The distal end of suturing instrument 45 is passed through a cannula and is placed at the surgical site. Handle (30) is pivoted away from handle (20) by the thumb so as to pivot movable member 55 such that grasping mechanism 51 is in its open position, as shown in FIG. 5, to enable grasping mechanism 51 to grasp a tissue to be sutured. With grasping mechanism 51 in the open orientation, the instrument is positioned such that a tissue to be sutured is placed within the gap between static member 52 and movable member 55.

Handle (30) is then pivoted towards handle (20) to pivot movable member 55 toward ribbed surface 53 causing mechanism 51 to move to its closed position (as shown in FIG. 4) in order to both grasp the tissue and position the suture on the side of the tissue. Closing mechanism 51 causes opening 59 to align with guide member (24). Handle (40) is then pivoted toward handle (20) with the index finger to move crochet head 61 in a linear path through a forward stroke from its retracted position at the proximal end of mechanism 51 to beyond suture holder 57. Handle (40) is then released to permit its spring bias to return crochet head 61 through a return stroke via the same linear oath back to its retracted position at the proximal end of mechanism 51. If necessary, the index finger in the loop of handle (40) could forcibly pivot handle (40) away from handle (20) causing crochet head 61 to return to its retracted position.

During the movement of crochet head 61 in the forward stroke, point 62 pierces and penetrates through the tissue grasped and thereafter passes between the suture within suture groove 58 and the circumference of opening 59. Crochet head 61 is thus moved sufficiently past the suture such that hook 63 engages the suture on the return stroke and draws it through the hole pierced through the tissue. Handle (30) is then pivoted away from handle (20) by the thumb to move mechanism 51 to its open position, and thereby to release the tissue. Thereafter, suturing instrument 45 may then be withdrawn from the cannula, drawing the suture with it.

The suturing instruments of the present invention offer a number of substantial advantages over previously described suturing devices. The first advantage is simplicity of construction. Both embodiments of the suturing instrument are of simple mechanical design and are fabricated from a relatively small number of moving parts. In addition, the suturing instruments of the present invention do not depend upon excessively close tolerances to function effectively.

Furthermore, the suturing instruments of the present invention may be employed with one hand; once the suture is deployed on the device, the tissue may be grasped and the suture completed solely by the movement of the fingers of one hand, leaving the other hand free.

Finally, the suturing instruments of the present invention provide a positive and reliable method of effecting a suture from a remote location, thus avoiding missed stitches, a limitation which plagues devices employing separate piercing and retracting elements.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually, indicated to be incorporated herein by reference. In addition, citation or identification of any reference in this application shall not be construed as an admission that such reference is available as prior art to the present invention.

What is claimed is:

1. A tissue suturing instrument comprising:
   (a) a tissue grasping mechanism including a static grasping member and a pivotal grasping member designed and configured for grasping a tissue, said pivotal grasping member carrying a suture holder for positioning a suture on a first side of said tissue grasped thereby;
   (b) a crochet head slidably carried by said static grasping member and slidable in a rectilinear path parallel to said static grasping member through a forward stroke and a return stroke, said crochet head being designed and configured for piercing through said tissue from a second side thereof during said forward stroke, engaging said suture following said piercing, and drawing said suture through said tissue during said return stroke; and
   (c) a frame assembly including a proximal section formed with a first handle and a distal section carrying said tissue grasping mechanism and said crochet head, said proximal section and said distal section being connected by an elongated shank.

2. The instrument of claim 1, wherein said suture holder is in the form of a wall carried by said pivotal grasping member at an angle thereto and formed with an opening through which said crochet head moves during said forward stroke.

3. The instrument of claim 1, wherein said static grasping member carries a guide for guiding the sliding movement of said crochet head through its forward and return strokes.

4. The instrument of claim 3, wherein the static grasping member is formed with a face having a ribbed surface for firmly grasping said tissue, said face facing the pivotal grasping member.

5. The instrument of claim 3, wherein said guide carried by said static grasping member for guiding said crochet head is of a U-shaped configuration.

6. The instrument of claim 3, wherein said suture holder is formed with an opening alignable with said guide when said grasping members grasp the tissue, for guiding said crochet head to engage said suture when said suture is positioned on said first side of said tissue.

7. The instrument of claim 1, wherein said tissue grasping mechanism is part of a tissue grasping assembly including a proximal section formed with a second handle pivotally mounted relative to said first handle, a distal section carrying said static grasping member and said pivotal grasping member, and a coupling between said second handle and said pivotable grasping member for pivoting said pivotable grasping member upon pivoting said second handle.

8. The instrument of claim 7, wherein said coupling includes a rod extending through said elongated shank of the frame assembly.

9. The instrument of claim 7, wherein said crochet head is part of a crochet head assembly including a proximal section formed with a third handle pivotally mounted relative to said first handle, a distal section carrying said crochet head, and a coupling between said third handle and said crochet head for moving said crochet head upon pivoting said third handle.

10. The instrument of claim 9, wherein said coupling includes a slide slidable with respect to said elongated shank of the frame assembly, said slide being aligned by a guide member with said suture holder.

11. The instrument of claim 9, wherein said crochet head is slidably mounted in proximity to said tissue grasping mechanism and is movable through said forward stroke from a retracted position at a proximal end of the tissue grasping mechanism to an extended position beyond a distal end of said tissue grasping mechanism, and through said return stroke back to said retracted position; said crochet head having a pointed end for piercing the tissue during the forward stroke, a shaped surface for engaging the suture, and a hook formation for drawing said suture through said tissue during said return stroke.

12. The instrument of claim 11, wherein said third handle is spring-biased to said retracted position.

13. The instrument according to claim 11, wherein one of said grasping members has a shaped surface effective to locate said tissue in alignment with said slidable crochet head during its forward and return strokes.

14. A method of applying a suture to tissue, comprising:
   (i) providing a tissue suturing instrument comprising (a) a tissue grasping mechanism including a static grasping member and a pivotally mounted grasping member designed and configured for grasping a tissue, said pivotal grasping member carrying a suture holder for positioning a suture on a first side of said tissue grasped thereby; (b) a crochet head slidably carried by said static grasping member and slidable in a rectilinear path parallel to said static grasping member through a forward stroke and a return stroke, said crochet head being designed and configured for piercing through said tissue from a second side thereof during said forward stroke, engaging said suture following said piercing, and drawing said suture through said tissue during said return stroke; and (c) a frame assembly including a proximal section formed with a first handle and a distal section carrying said tissue grasping mechanism and said crochet head, said proximal section and said distal section being connected by an elongated shank.
   (ii) applying a suture to said suture holder such that the suture is on one side of the tissue to be sutured, and said static grasping member and crochet head carried thereon are on the opposite side of the tissue to be sutured;
   (iii) pivotting said first handle to cause said crochet head to move rectilinearly from said opposite side to said one side, to pierce said grasped tissue, and to engage said suture on said one side; and (iv) returning said first handle to cause the crochet head to move rectilinearly with the suture from said one side to said opposite side.

15. The method according to claim 14, wherein the static grasping member is formed with a face having a ribbed surface for firmly grasping said tissue, said face facing the pivotable member.

16. The method according to claim 14, wherein said static grasping member is formed with a guide member disposed thereon for guiding said crochet head.

17. The method according to claim 16, wherein said suture holder is in the form of a wall carried by said static grasping member at an angle thereto and formed with an opening through which said crochet head moves during said forward stroke.

18. The method according to claim 14, wherein said tissue grasping mechanism is part of a tissue grasping assembly including a proximal section formed with a second handle pivotally mounted relative to said first handle, a distal section carrying said static grasping member and said pivotal grasping member, and a coupling between said second handle and said pivotal member for pivoting said pivotable member upon pivoting said second handle.

* * * * *